United States Patent [19]

Munteanu

[11] Patent Number: 4,915,301
[45] Date of Patent: Apr. 10, 1990

[54] CONTAINER WITH SORBENT MEMBER AND MICROPOROUS MEMBRANE FOR DISPENSING VAPOR FROM VOLATILE LIQUID

[75] Inventor: Marina A. Munteanu, New York, N.Y.

[73] Assignee: International Flavors & Fragrances, Inc., New York, N.Y.

[21] Appl. No.: 271,628

[22] Filed: Nov. 15, 1988

[51] Int. Cl.$^4$ ................................................ A61L 9/04
[52] U.S. Cl. ...................................... 239/45; 239/54; 239/55
[58] Field of Search ................. 239/34, 45, 47, 49, 239/50, 51.5, 54, 55, 56, 37

[56] References Cited

U.S. PATENT DOCUMENTS

| Re. 32,513 | 10/1987 | Seaber et al. |
|---|---|---|
| 859,183 | 7/1907 | Sprague et al. ................ 239/37 |
| 1,129,897 | 3/1915 | Owen, Jr. ........................ 239/45 |
| 2,766,069 | 10/1956 | Tennyson ........................ 239/43 |
| 4,387,849 | 6/1983 | Van Loveren et al. |
| 4,400,311 | 8/1983 | Klemarczyk et al. .......... 252/522 |
| 4,413,779 | 11/1983 | Santini ............................ 239/45 |
| 4,466,931 | 8/1984 | Tanny |
| 4,605,165 | 8/1986 | Van Loveren et al. |
| 4,614,299 | 9/1986 | Van Loveren et al. |
| 4,725,644 | 2/1988 | Malhotra |
| 4,742,086 | 5/1988 | Masamizu et al. |
| 4,743,327 | 5/1988 | DeHaan et al. |
| 4,761,233 | 8/1988 | Linder et al. |
| 4,761,234 | 8/1988 | Uemura et al. |
| 4,767,808 | 8/1988 | Kydonieus et al. |
| 4,775,551 | 10/1988 | Bachot et al. |
| 4,775,703 | 10/1988 | Susa |

FOREIGN PATENT DOCUMENTS

| 1242556 | 10/1988 | Canada. |
|---|---|---|
| 0238276 | 9/1987 | European Pat. Off. |
| 0260896 | 3/1988 | European Pat. Off. ............ 239/34 |
| 0273763 | 7/1988 | European Pat. Off. |
| 686329 | 3/1965 | Italy ................................ 239/56 |
| 8800205 | 8/1988 | PCT Int'l Appl. |
| 8800237 | 8/1988 | PCT Int'l Appl. |

OTHER PUBLICATIONS

Shafrin, E. G. "Critical Surface Tensions of Polymers", in: *Polymer Handbook*, 2nd ed. Wiley Interscience, 1975, pp. III-221-III-228.

Haggin, Joseph, "Membranes Play Growing Role in Small-Scale Industrial Processing", Chemical & Engineering News, vol. 66, No. 28 (Jul. 11, 1988), pp. 25-32.

Pierlot, C. et al., "Pervaporation de volatils a traverse une membrane microporeuse," *Entropie*, No. 137/138 (1987), pp. 57-62.

"U.V./E.B. Polymerized Microporous Membranes", Gelman Sciences, published bulletin, date unknown.

*Primary Examiner*—Andres Kashnikow
*Assistant Examiner*—Michael J. Forman
*Attorney, Agent, or Firm*—Brooks Haidt Haffner & Delahunty

[57] ABSTRACT

Volatile substances such as fragrances, perfumes, deodorizers, room freshener compositions and the like are dispensed in vapor phase from a container holding the substance in liquid phase at room temperature and under atmospheric pressure. The container has a window covered with a microporous membrane with an active structure formed from a material having a critical surface tension that is below the surface tension of the liquid substance. Generally the active membrane material has a critical surface tension that is below 22 dynes/cm and preferably below 20 dynes/cm while the surface tension of the liquid is at least 22 dynes/cm. One example is an ultraviolet irradiated polymer composition with 0.2 microns nominal pore size. In all instances the volatile substance is first sorbed within a porous element and desorbed therefrom for transport through the membrane only in its vapor phase.

30 Claims, 2 Drawing Sheets

CONTAINER WITH SORBENT MEMBER AND MICROPOROUS MEMBRANE FOR DISPENSING VAPOR FROM VOLATILE LIQUID

BACKGROUND OF THE INVENTION

The present invention relates to apparatus for packaging and dispensing a volatile substance to be dispensed in a vapor phase. In particular, it relates to apparatus for dispensing air fresheners, aromatizing agents, deodorizers, odor maskents, insect repellents, animal repellents, pheromones and combinations thereof.

Numerous vapor releasing devices have been described in the literature and manufactured heretofore. In some, the vaporizable substance is incorporated in a solid carrier medium from which it gradually evaporates and enters the atmosphere once a protective wrap or enclosure is breached or removed. In others, the substance is packaged in liquid form and vaporized in some manner to discharge into the atmosphere.

One type of room freshener is known wherein an aromatic liquid is packaged in a container provided with a wick immersed in the liquid and communicating with a porous member having a broad evaporation promoting surface. Unfortunately, the surface of the porous member tends to discolor rendering the device both less effective and unattractive. This drawback has also placed a restriction upon the substances that can be dispensed in this fashion because certain substances tend to discolor the porous member more than others. In addition, the presence of liquid on the exterior surface creates a number of problems since the liquid can be an irritant if carried to the eyes of an individual, the liquid can soil clothing, and can otherwise cause undesirable soiling.

Certain of the prior art devices have employed microporous membranes. Thus in Van Loveren et al. U.S. Pat. No. 4,387,849 there is described a hollow container comprising a shell which is at least partially porous, containing an entrapped volatile substance. The substance is entrapped in a gel and is, in the alternative, a perfume composition, a deodorant composition, an air freshener composition, an insecticide composition, a herbicide composition, an odor masking composition, a pheromone composition, an animal repellent composition, or an insect repellent composition. The container containing the entrapped volatile substance ceases to discharge into the atmosphere when placed in an outer air-tight container. Said patent refers to various microporous polymers giving as examples a polypropylene and filler composition, a polyurethane and filler composition, a composition of polyvinyl alcohol and xanthan gum, and a cyclodextrin and activated silicate composition. The patent also mentions production of a microporous film by heating a mixture of synthetic thermoplastic polymer which may be a polymer or a copolymer of an ethylenically unsaturated monomer, condensation polymer, polyphenylene oxide or a blend thereof and a compatible liquid to a temperature and for a time sufficient to form a homogeneous solution, allowing the solution to assume a desired shape and cooling the solution to initiate liquid-liquid phase separation followed by cooling to solidify the film.

The Van Loveren et al. patent also describes a number of structural embodiments. The embodiment illustrated in its FIGS. 5 and 7, for example, takes the form of a right circular cylinder with microporous walls, the cylinder containing the fragrance bearing gel which cylinder is packaged in an outer vial provided with a screw cap top. While the entire side wall of the cylinder is illustrated as microporous, the patent states that not all of the side wall need be so fabricated. Instead, merely the upper third or the upper quarter or the lower quarter of the side wall or even the top or the bottom of the cylindrical container may be fabricated from microporous polymer, the remainder of the cylinder shell being fabricated using a transparent substance which is rigid or flexible or using a silicate or quartz glass.

Experience with all of the microporous membranes mentioned in the Van Loveren et al. patent indicates that a captivating medium such as the disclosed gels is essential to prevent the volatile substance from wetting the microporous membrane and even forming droplets on its outer surface. This can stain and damage anything that comes in contact with it.

SUMMARY OF THE INVENTION

With the foregoing as background it is an object of the present invention to provide apparatus for packaging and dispensing a volatile substance where the substance can be packaged in liquid form without causing discoloration of any visible part of the package during use. It is a further object to provide a vapor dispensing container which never becomes wet to the touch on its exterior surfaces yet efficiently emits vapors from a liquid charge maintained at atmospheric pressure.

In accordance with one aspect of the present invention there is provided apparatus for packaging and dispensing a volatile substance stored in a liquid phase and dispensed in a vapor phase where the apparatus comprises a container for confining at atmospheric pressure and room temperature a quantity of a volatile substance that is liquid at atmospheric pressure and room temperature and has a surface tension in its liquid phase that is above a predetermined value. The container is formed by first and second wall portions, the first wall portion being essentially impervious to the substance. The second wall portion includes a microporous membrane having interior and exterior surfaces with the exterior surface exposable to the atmosphere surrounding the container. The membrane has an active structure formed from a material that lacks affinity for the substance which material has a critical surface tension that is below the predetermined value of surface tension mentioned above. The membrane has an air flow permeance such that when the exterior surface of the membrane is exposed to the atmosphere the substance is transported through the second portion and discharged into the atmosphere as a vapor while the exterior surface of the second portion remains dry to the touch, and at least one body within said container having a porous structure within which said substance is sorbed and subsequently desorbed for said transport through said membrane.

BRIEF DESCRIPTION OF THE DRAWINGS

The invention will be better understood after reading the following detailed description of the presently preferred embodiments thereof with reference to the appended drawings in which.

DETAILED DESCRIPTION OF THE PRESENTLY PREFERRED EMBODIMENTS

The present invention arises from the discovery that a certain type of microporous membrane, when placed in contact with liquid substances of the type used to provide aromatic vapors, will enable emission of the vapors of the substance while preventing passage of the liquid, at least to the extent that droplets do not reach the exposed surface of the membrane and the exposed surface remains dry to the touch. A membrane that has been found satisfactory for the purposes of the present invention consists essentially of a porous supporting substrate supporting a coating layer of a microporous polymer. The membrane is manufactured by Gelman Sciences Technology Ltd. of Ann Arbor, Michigan, and marketed under their "Sunbeam Process" trademark as "REPEL Microporous Membrane" Such membrane has a substrate in the form of a nonwoven polyester sheet, while the coating layer is formed from a thin film layer of a microporous polymer. According to the manufacturer, the membrane is produced using the process described in U.S. Pat. No. 4,466,931, issued Aug. 21, 1984, incorporated herein by reference. Said patent describes use of ultraviolet irradiation or the like for promoting polymerization of the resin. However, the production of the membrane does not constitute a part of the present invention and will not be described in further detail.

A sample membrane from Gelman Sciences was specified by the manufacturer as having a nominal pore size of 0.2 microns a coating weight of 23.6 gm/m$^2$, an air flow characteristic of 110 ml/min cm$^2$ at 80 cm H$_2$O, and a water break through pressure greater than 4.5 kg/cm$^2$. Another sample was specified as having a nominal pore size of 0.2 microns, a coating weight of 25 gm/m$^2$, an air flow characteristic of 100 ml/min cm$^2$ at 80 cm H$_2$O, a water break through pressure at least as great as 4 kg/cm$^2$, and a bubble point for kerosene of at least 2 atmospheres. Both samples were essentially solventphobic.

As a general requirement for the present invention, the active membrane layer should be fabricated from a material that lacks affinity for the liquid substance whose vapor is to pass the membrane. In addition, the membrane material should have a critical surface tension that is no greater than 22 dynes/cm and preferably no greater than 20 dynes/cm. Consequently, so long as the surface tension of the liquid substance exceeds the 22 dynes/cm value it will not wet the active layer and pass through as a liquid. As will appear below, the liquid substances generally have a surface tension characteristic of at least 22 dynes/cm.

The instant discovery enables modification of an entire family of dispensers that serve as both the package for containing the liquid substance and the dispenser therefor. A few typical embodiments will now be described.

Figure 1:
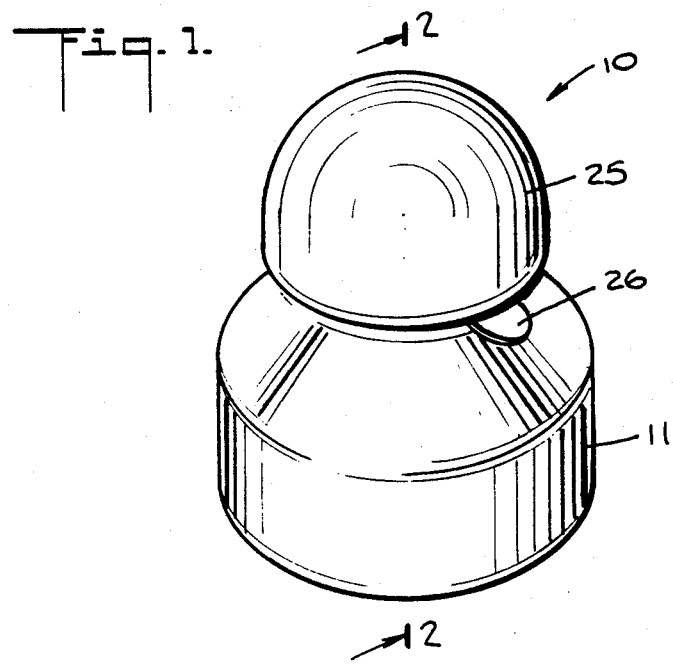
FIG. 1 is a perspective view of a container for an aromatizing substance representing one embodiment of the present invention.
Figure 2:
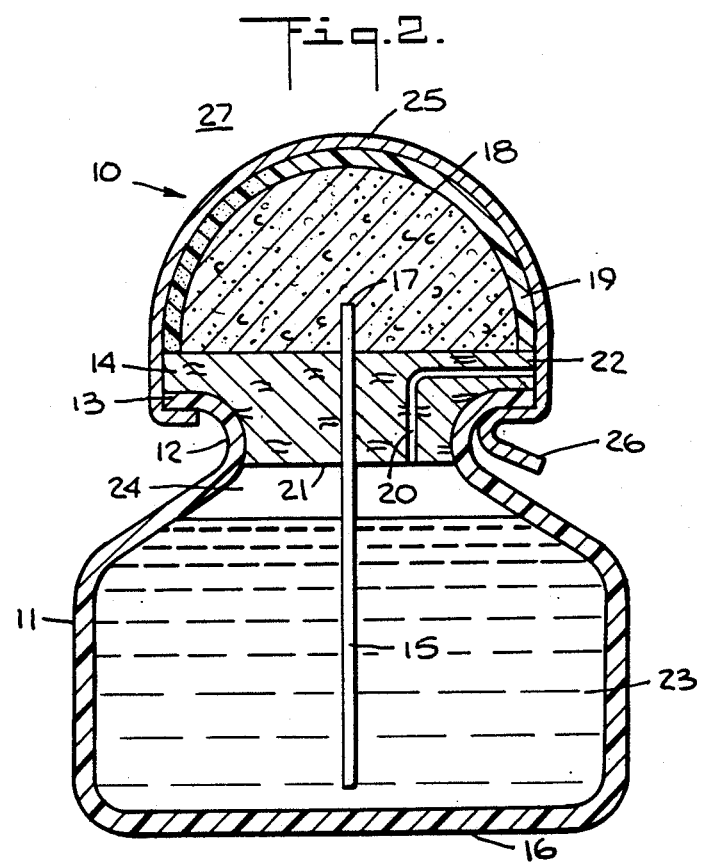
FIG. 2 is a vertical sectional view of the container embodiment of FIG. 1 taken along the line 2—2 in FIG. 1.
Figure 3:
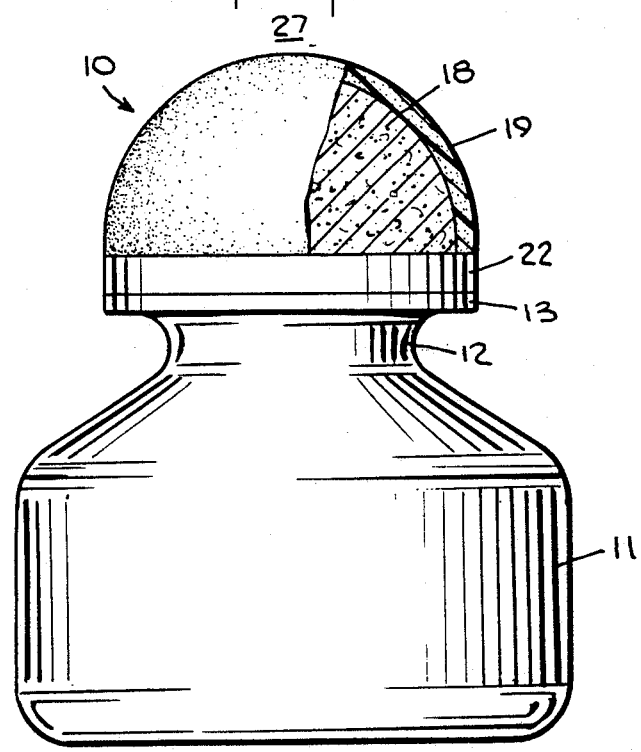
FIG. 3 is a front elevational view of the container of FIG. 1 with the top seal removed and a portion broken away.

Reference should be had to FIGS. 1 to 3 wherein a liquid container 10 is shown as formed from a bottle 11, preferably fabricated from a suitable plastic, having a reduced diameter neck 12 terminating in a radially outwardly extending flange 13. A stopper 14 of cork or other suitable material plugs the opening in the neck 12 and suspends a length of wick 15 into the bottle 11 down to close to the bottle bottom 16. The wick 15 has an upper end 17 imbedded in the base of a somewhat hemispherically shaped porous body 18 that is secured to the outer surface of the stopper 14. Overlying the outer surface of the body 18 is a microporous membrane 19 having an active structure with a critical surface tension below 22 dynes/cm.

As best seen in FIG. 2, the stopper 14 has a vent passage 20 formed therein which extends from the stopper inner surface 21 upwardly, as viewed in the drawing, and then radially outwardly to the edge 22 of the stopper 14 that overlies the bottle flange 13. After filling the bottle 11 with an aromatizing or other volatile liquid 23, except for a small space 24 to allow for expansion, the stopper 14, with wick 15 attached, is inserted in bottle neck 12. Thereafter the dispenser is sealed by covering the membrane 19 and stopper 14 with a piece of foil 25 that extends down and under bottle flange 13 where it is adhesively secured by any suitable bonding agent. The foil 25 includes a projecting tab portion 26 to facilitate removal of the foil when it is desired to dispense the packaged liquid.

When the bottle 11 contains the liquid 23, the liquid substance 23 will be sorbed by wick 15 and conveyed to the bottom of porous body 18 where it is sorbed and spread throughout the hemisphere. When the seal 25 is removed, any of the substance 23 that reaches the interface between porous body 18 and membrane 19 will pass through the membrane 19 to be discharged as a vapor into the atmosphere 27. See FIG. 3 where the foil 25 has been removed. With the foil 25 removed there will exist a continual transport of the substance 23 up the wick 15, through the hemisphere 18 and through the membrane 19. This action is aided by air entering the space 24 through passage 20.

The membrane 19 can be thought of as akin to a window permitting only the vapor phase of the volatile substance to exit the container. But the liquid cannot wet the membrane material and, therefore, does not appear on the exterior surface in its liquid phase. Consequently, the surface of the membrane 19 is dry to the touch and does not discolor, regardless of the concentration or susceptibility to discoloration of the volatile substance.

Before considering another embodiment of the invention, it will be helpful to have an understanding of the liquids that are to be used with the subject packaging. In essence, it has been found that any volatile liquid can be dispensed in the manner of the invention if its surface tension exceeds the critical surface tension of the material from which the microporous membrane is constructed. This assumes, of course, that the materials of the container and the liquid are compatible and mutually inert.

A typical room freshener or aromatizing composition for use with a container with a microporous window has the following composition:

EXAMPLE I

| INGREDIENT | % BY WEIGHT |
| --- | --- |
| Fragrance** | 3.00 |
| Triton X 100* | 7.00 |
| SDA 39C Alcohol | 23.00 |
| Deionized Water | 67.00 |

*Octoxynol-9 (Rohm & Haas)

**FRAGRANCE

| INGREDIENT | PARTS BY WEIGHT |
| --- | --- |
| Terpineol | 448 |
| Hydroxy citronellal | 133 |
| Heliotropin | 160 |
| Phenylethyl alcohol | 50 |
| Benzyl Acetate | 82 |
| Anisaldehyde | 95 |
| Oil of cananga | 6 |
| Coumarin | 3 |
| Alpha ionone | 6 |
| Methyl jasmonate | 8 |
| 2,3-dimethyl-hydroquinone | 6 |
| p-methoxy acetophenone | 3 |
| Mixture of substituted isopropyl methyl cyclohexenones | 35 |

For a more detailed description of the composition and of other compositions, reference should be had to U.S. Pat. No. 4,400,311. In particular, said patent contains a description of the method of preparing the mixture of substituted isopropyl methyl cyclohexenones.

In the construction of the dispenser illustrated in FIGS. 1 to 3, the porous body 18 should have an affinity for and be wet by the liquid substance being dispensed. In particular, the body 18 should have a critical surface tension at least as great as and preferably above the surface tension of the liquid substance to be dispensed. With the foregoing caveat, the body 18 can be fabricated from pressed paper, i.e., cardboard, pressed cotton, pressed cellulose fiber, ceramics, gypsum, sand plus cement, pressed sawdust, porous polymers, porous polyethylene, porous polypropylene, porous polyesters, or any other material capable of sorbing the liquid substance and transporting it to the interface with the membrane 19.

Figure 4:
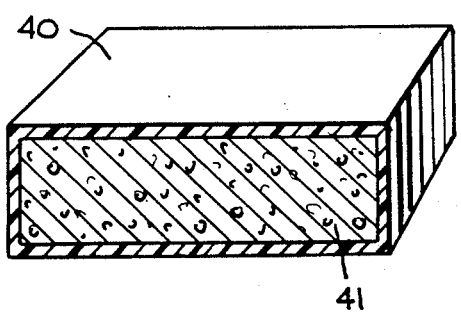
FIG. 4 is a perspective view with a section broken away of another embodiment of the invention wherein the porous body is enveloped within a microporous membrane. Throughout the drawings the same reference numerals are used to designate the same or similar parts.

Referring now to FIG. 4, there is illustrated another embodiment of the invention wherein a microporous membrane 40 completely envelopes a porous body 41 that has been saturated with the liquid substance to be dispensed. The envelope 40 should encapsulate the body 41 which can have any appropriate three dimensional configuration. The encapsulated structure as shown in FIG. 4 is exposed for discharging vapors of the substance into the surrounding atmosphere 42. For packaging until ready for use, a foil wrapper will enclose the envelope 40 sealing the substance within.

Reflecting upon the embodiments of FIGS. 1 to 4, it should be apparent that the membranes 19 and 40 are interposed between the body 18 or 41 containing the stock volatile substance and the atmosphere 27, 42 surrounding the respective container. In each case it prevents any of the volatile substance from reaching the exterior of the container in its liquid state and thereby prevents staining and discoloration.

The foregoing description describes the container 10 as having a base element 11 defined by wall portions that are essentially impervious to the liquid substance to be packaged therein. In addition, the material of which such wall portions are constructed must not adversely react with the liquid volatile substance. Obviously, it should have sufficient strength and rigidity to function as required. It is believed that selection of the appropriate materials is well within the knowledge and scope of those skilled in the relevant art. Among suitable materials are glass, certain metals, and nonporous plastic such as polyethylene.

The window or second wall portion in the embodiment of FIGS. 1 to 3 is constructed of a microporous membrane with the requirement that the nominal pore size fall within the range of 0.1 to 5 microns with a 0.2 micron nominal pore size being presently preferred. Satisfactory membranes have a nominal total thickness of 30 to 600 microns with a substrate nominal thickness of 15 to 300 microns and a microporous layer nominal thickness of 15 to 300 microns.

The volatile liquid substances that can be packaged and dispensed using the embodiments described herein are those ranging in surface tension from 22 to 72 dynes/cm and encompass substantially all volatile perfumes, air freshener compositions, deodorizers, animal repellents, insect repellents, and pheromone compositions and combinations thereof.

The microporous membranes must be fabricated from a material that has a critical surface tension that is below the surface tension of the liquid. With the liquid surface tensions ranging from 22 to 72 dynes/cm, the membrane critical surface tension should be below 22 and preferably no greater than 20 dynes/cm. At present it is preferred to select the membrane active material from the group consisting essentially of poly fluoro compounds, polyimines, polybutadienes, copolymers of fluoro vinyl compounds with ethylene, and copolymers of fluoro vinyl compounds with acrylates.

As used throughout this specification, critical surface tension, applied to solid materials, serves to define the wettability of a surface of the solid by noting the lowest surface tension a liquid can have and still exhibit a contact angle greater than zero degrees on that solid. For a discussion of this constant, reference can be had to the section entitled "Critical Surface Tensions of Polymers" by E. G. Shafrin appearing in *Polymer Handbook*, 2nd ed., Brandrup and Immergut eds., published by Wiley Interscience, 1975, p. III-221.

Having described the present invention with reference to the presently preferred embodiments thereof, it should be apparent to those skilled in the subject art that various changes in construction can be introduced without departing from the true spirit of the invention as defined in the appended claims.

What is claimed is:

1. Apparatus for packaging and dispensing a volatile substance stored in a liquid phase and dispensed in a vapor phase, said apparatus comprising a container for confining at atmospheric pressure and room temperature a quantity of a volatile substance that is liquid at atmospheric pressure and room temperature and has a surface tension in its liquid phase that is above a predetermined value, said container being formed by first and second wall portions, said first wall portion being essentially impervious to said substance and including means for establishing communication between the interior of the container and the atmosphere when it is desired to dispense said substance, said second wall portion including a microporous membrane having interior and exterior surfaces with the exterior surface exposable to the atmosphere surrounding said container, said membrane having an active structure formed from a material that lacks affinity for said substance and has a critical surface tension that is below said predetermined value, said membrane having an air flow permeance such that when said exterior surface is exposed to the atmosphere said substance is transported through said second portion and discharged into the atmosphere as a vapor while said exterior surface of said second portion remains dry to the touch, and at least one body within said container having a porous structure within which said volatile substance is sorbed and subsequently desorbed for said transport through said membrane.

2. Apparatus according to claim 1, wherein said predetermined value of surface tension of said liquid is at least 22 dynes/cm.

3. Apparatus according to claim 2, wherein said surface tension of said liquid is in the range of 22 to 72 dynes/cm.

4. Apparatus according to claim 3, wherein said material of said membrane has a critical surface tension that is less than 22 dynes/cm.

5. Apparatus according to claim 4, wherein said material of said membrane is a fluorocarbon resin.

6. Apparatus according to claim 5, wherein said membrane has a nominal pore size of about 0.2 microns and an air transmission rate ringing from about 100 to about 110 ml/min/$cm^2$ at 80 cm water column pressure.

7. Apparatus according to claim 4, wherein said active structure of said membrane comprises a microporous body formed from a material selected from the group consisting essentially of poly fluoro compounds, polyimines, polybutadienes, copolymers of fluoro vinyl compounds with ethylene, and copolymers of fluoro vinyl compounds with acrylates.

8. Apparatus according to claim 3, wherein said active structure of said membrane comprises a microporous body formed from a material selected from the group consisting essentially of poly fluoro compounds, polyimines, polybutadienes, copolymers of fluoro vinyl compounds with ethylene, and copolymers of fluoro vinyl compounds with acrylates.

9. Apparatus according to claim 3, wherein said active structure is a microporous membrane through which only the vapor phase of said substance can pass where said substance is a volatile composition selected from the group consisting of perfume, air freshening, deodorizing, animal repellent, insect repellent, and pheromone compositions and combinations thereof.

10. Apparatus according to claim 9, wherein said material of said active structure is a fluorocarbon resin.

11. Apparatus according to claim 2, wherein said material of said membrane has a critical surface tension that is less than 22 dynes/cm.

12. Apparatus according to claim 1, wherein said material of said membrane is a fluorocarbon resin.

13. Apparatus according to claim 12, wherein said membrane has a nominal pore size of about 0.2 microns and an air transmission rate ranging from about 100 to about 110 ml/min/$cm^2$ at 80 cm water column pressure.

14. Apparatus according to claim 12, wherein said membrane comprises a support substrate, and said active structure comprises a microporous polymer layer supported on said substrate.

15. Apparatus according to claim 14, wherein said microporous polymer comprises a material selected from the group consisting essentially of poly fluoro compounds, polyimines, polybutadienes, copolymers of fluoro vinyl compounds with ethylene, and copolymers of fluoro vinyl compounds with acrylates.

16. Apparatus according to claim 1, wherein said active structure of said membrane comprises a microporous body formed from a material selected from the group consisting essentially of poly fluoro compounds, polyimines, polybutadienes, copolymers of fluoro vinyl compounds with ethylene, and copolymers of fluoro vinyl compounds with acrylates.

17. Apparatus according to claim 1, wherein said active structure is a microporous membrane through which only the vapor phase of said substance can pass where said substance is a volatile composition selected from the group consisting of perfume, air freshening, deodorizing, animal repellent, insect repellent, and pheromone compositions and combinations thereof.

18. Apparatus according to claim 1, wherein said membrane comprises a support substrate, and said active structure comprises a microporous polymer layer supported on said substrate.

19. Apparatus according to claim 18, wherein said microporous polymer comprises a material selected from the group consisting essentially of poly fluoro compounds, polyimines, polybutadienes, copolymers of fluoro vinyl compounds with ethylene, and copolymers of fluoro vinyl compounds with acrylates.

20. Apparatus according to claim 1, wherein said active structure of said membrane comprises a microporous body formed from a material selected from the group consisting essentially of poly fluoro compounds, polyimines, polybutadienes, copolymers of fluoro vinyl compounds with ethylene, and copolymers of fluoro vinyl compounds with acrylates.

21. Apparatus according to claim 1, wherein said active structure is a microporous membrane through which only the vapor phase of said substance can pass where said substance is a volatile composition selected from the group consisting of perfume, air freshening, deodorizing, animal repellent, insect repellent, and pheromone compositions and combinations thereof.

22. Apparatus according to claim 21, wherein said material of said active structure is a fluorocarbon resin.

23. Apparatus according to claim 1, wherein said substance is an aromatizing composition.

24. Apparatus according to claim 1, wherein said body with a porous structure is disposed within said container with a first portion of said body immersed in a quantity of said liquid substance, and another portion of said body projecting from said liquid substance and extending into proximity with said membrane whereby said body operates, when said apparatus is dispensing, as a wick conveying said liquid substance to the vicinity of said membrane for said transport therethrough.

25. Apparatus for packaging and dispensing a volatile substance that is liquid at atmospheric pressure and room temperature and has a surface tension in its liquid phase that is above a predetermined value, said substance being stored in a liquid phase and dispensed in a vapor phase, said apparatus comprising a container, at least one body within said container having a porous structure within which said volatile substance is at least partially sorbed, and an opening through a wall of said container which opening is covered over by a microporous membrane having interior and exterior surfaces with the exterior surface exposable to the atmosphere surrounding said container, said membrane having an active structure formed from a material that lacks affinity for said substance and has a critical surface tension that is below said predetermined value, said membrane having an air flow permeance such that when said exterior surface of said membrane is exposed to the atmosphere said volatile substance is transported through said membrane and discharged into the atmosphere as a vapor while said exterior surface of said membrane remains dry to the touch.

26. Apparatus according to claim 25, wherein said body with a porous structure is disposed within said container with a first portion of said body immersed in a quantity of said volatile substance, and another portion of said body projecting from said volatile substance and extending into proximity with said membrane whereby said body operates, when said apparatus is dispensing, as a wick conveying said volatile substance to the vicinity of said membrane for said transport therethrough.

27. Apparatus according to claim 25, wherein said volatile substance is sorbed by and wholly contained within said body with a porous structure from which, during dispensing, said volatile substance desorbs with evaporation to be transported through said membrane.

28. Apparatus according to claim 27, wherein said body is sponge-like and completely enveloped by said container.

29. Apparatus for packaging and dispensing a volatile substance that is liquid at atmospheric pressure and room temperature and has a surface tension in its liquid phase that is above a predetermined value, said substance being stored in a liquid phase and dispensed in a vapor phase, said apparatus comprising a container, at least one body within said container having a porous structure within which said volatile substance is at least partially sorbed, said container having walls at least a portion of which consists of a microporous membrane located inbetween said body and the atmosphere surrounding said container, said microporous membrane having interior and exterior surfaces with the exterior surface exposable to the atmosphere surrounding said container, said membrane having an active structure formed from a material that lacks affinity for said substance and has a critical surface tension that is below said predetermined value, said membrane having an air flow permeance such that when said exterior surface of said membrane is exposed to the atmosphere said volatile substance is transported through said membrane and discharged into the atmosphere as a vapor while said exterior surface of said membrane remains dry to the touch.

30. Apparatus according to claim 29, wherein said microporous membrane completely envelopes said porous structure body.

* * * * *